United States Patent
Jensen

(10) Patent No.: US 9,814,477 B2
(45) Date of Patent: Nov. 14, 2017

(54) CLOT RETRIEVAL SYSTEM WITH INVERTED SLEEVE

(71) Applicant: Cook Medical Technologies LLC, Bloomington, IN (US)

(72) Inventor: Anders Ginge Jensen, Hornslet (DK)

(73) Assignee: Cook Medical Technologies LLC, Bloomington, IN (US)

( * ) Notice: Subject to any disclaimer, the term of this patent is extended or adjusted under 35 U.S.C. 154(b) by 450 days.

(21) Appl. No.: 14/454,039

(22) Filed: Aug. 7, 2014

(65) Prior Publication Data

US 2015/0088190 A1 Mar. 26, 2015

Related U.S. Application Data

(60) Provisional application No. 61/881,633, filed on Sep. 24, 2013.

(51) Int. Cl.
| | |
|---|---|
| A61F 2/01 | (2006.01) |
| A61B 17/3207 | (2006.01) |
| A61B 17/22 | (2006.01) |
| A61B 17/12 | (2006.01) |

(52) U.S. Cl.
CPC .. *A61B 17/22032* (2013.01); *A61B 17/12109* (2013.01); *A61B 17/3207* (2013.01); *A61F 2/01* (2013.01); *A61B 2017/22034* (2013.01); *A61B 2017/22035* (2013.01); *A61B 2017/320741* (2013.01); *A61F 2230/0071* (2013.01)

(58) Field of Classification Search
CPC .......... A61B 17/22032; A61B 17/3207; A61B 2017/320716; A61B 2017/22034; A61B 2017/22035; A61B 2017/22051; A61B 2017/22052; A61B 2017/22054; A61B 2017/22067; A61B 2017/22068; A61B 2017/22069; A61B 2017/22071; A61B 2017/22065; A61F 2/01; A61F 2002/011; A61F 2/013; A61F 2002/015
USPC ................................ 623/1.11, 2.11; 606/200
See application file for complete search history.

(56) References Cited

U.S. PATENT DOCUMENTS

| | | | |
|---|---|---|---|
| 6,840,950 B2 | 1/2005 | Stanford et al. | |
| 8,430,901 B2 | 4/2013 | Gilson et al. | |
| 2003/0100918 A1* | 5/2003 | Duane .............. | A61B 17/12022 606/200 |

(Continued)

FOREIGN PATENT DOCUMENTS

| | | |
|---|---|---|
| WO | 2012049652 | 4/2012 |
| WO | 2012162437 | 11/2012 |

*Primary Examiner* — Eric Rosen
*Assistant Examiner* — Chima Igboko
(74) *Attorney, Agent, or Firm* — Liell & McNeil

(57) ABSTRACT

A clot retrieval system includes a delivery catheter defining a lumen and having proximal and distal ends. An elongate shaft has proximal and distal ends and is configured for receipt within the delivery catheter. An inverted sleeve has a closed end attached to a distal segment of the elongate shaft and an open end. An outer section of the inverted sleeve that includes the open end is folded over onto an inner section of the inverted sleeve that includes the closed end at a rolling fold. An expansion device is supported on the elongate shaft at an axial location proximally spaced from the closed end and aligned with or distally spaced from the open end. The expansion device is configured for radially expanding the open end of the inverted sleeve.

20 Claims, 2 Drawing Sheets

(56) References Cited

U.S. PATENT DOCUMENTS

| | | | |
|---|---|---|---|
| 2003/0105484 A1* | 6/2003 | Boyle | A61F 2/013 606/200 |
| 2003/0176884 A1* | 9/2003 | Berrada | A61F 2/013 606/200 |
| 2005/0038468 A1* | 2/2005 | Panetta | A61F 2/013 606/200 |
| 2006/0009784 A1 | 1/2006 | Behl et al. | |
| 2007/0088382 A1 | 4/2007 | Bei et al. | |
| 2007/0288054 A1 | 12/2007 | Tanaka et al. | |
| 2009/0287193 A1 | 11/2009 | Desai et al. | |
| 2009/0299393 A1 | 12/2009 | Martin et al. | |
| 2010/0249815 A1 | 9/2010 | Jantzen et al. | |
| 2012/0083824 A1 | 4/2012 | Berrada et al. | |
| 2012/0150110 A1 | 6/2012 | Chin | |

\* cited by examiner

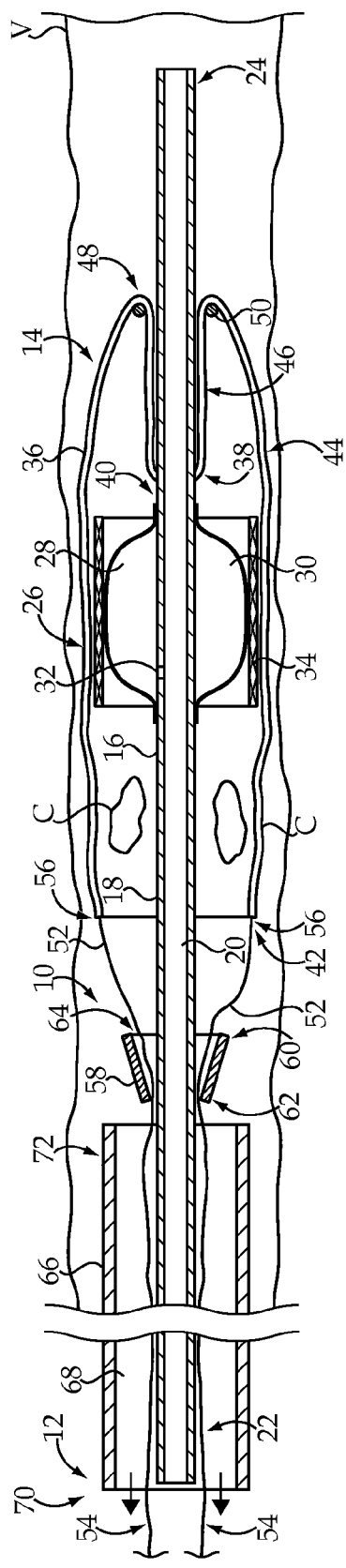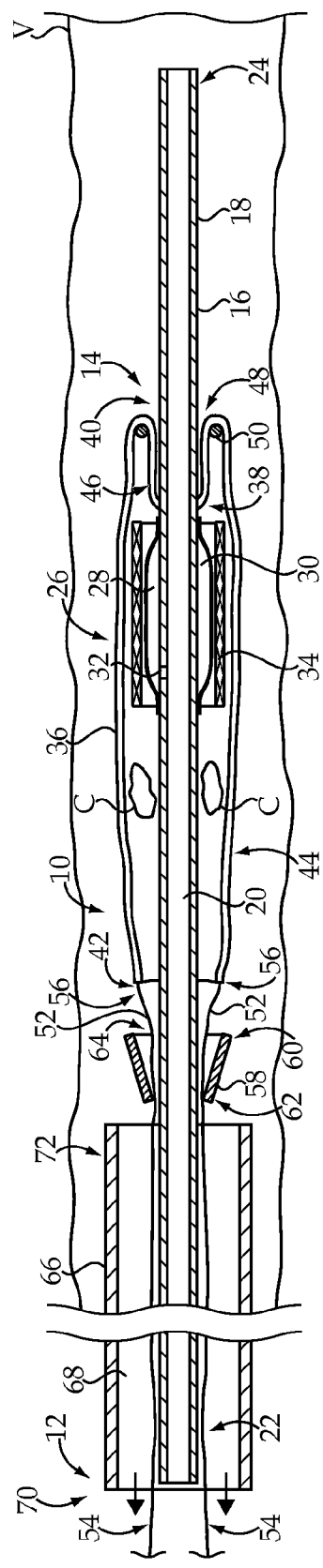
Fig.3
Fig.4

CLOT RETRIEVAL SYSTEM WITH INVERTED SLEEVE

TECHNICAL FIELD

The present disclosure relates generally to a clot retrieval system, and more particularly to a clot retrieval system including an inverted sleeve having an open end that is radially expanded at a position distal to a clot and then proximally retracted to capture the clot.

BACKGROUND

Thrombosis is the formation of a thrombus, or blood clot, within the vascular system of a patient. A blood clot typically occurs when blood hardens from a liquid to a solid. When attached to vessel walls, blood clots, and other substances, such as plaque or fat, may reduce or block blood flow downstream from the clot. This partially or completely blocked blood flow may prevent normal blood flow and oxygen from reaching certain tissues and, thus, may result in damage to the tissues. If a clot becomes dislodged from the vessel walls it may travel to other portions of the vascular system, where it may ultimately occlude critical blood flow. Regardless of the particular location of the clot within the vascular system, clots consisting of blood or other substances, if left untreated, may cause serious damage and, in some cases, may become life threatening.

A wide variety of invasive and non-invasive techniques are available for breaking up and/or removing clots within the vascular system. For example, some techniques include the use of pharmacological agents, also referred to as thrombolytic agents, to help dissolve the clots. Other techniques may include the use of mechanical agitation to dislodge clots from walls of the vascular system and/or a device for capturing clots. For example, a device described in U.S. Patent Application Publication No. 2010/0249815 to Jantzen et al. teaches a device for breaking down and capturing a thrombus. The device includes an inner catheter disposed within an outer sheath. The device also includes a rollsock that is everted upon itself and connected to the distal ends of the outer sheath and inner catheter. A scraping device is attached to the outer surface of the rollsock such that when the outer sheath is moved relative to the inner catheter the scraping device is exposed to an inner surface of a body vessel. Although this device may prove effective in particular procedures, there is a continuing need for clot removal systems that are effective and that offer reduced risks.

The present disclosure is directed toward one or more of the problems or issues set forth above.

SUMMARY OF THE DISCLOSURE

In one aspect, a clot retrieval system includes a delivery catheter defining a lumen and having proximal and distal ends. An elongate shaft has proximal and distal ends and is configured for receipt within the delivery catheter. An inverted sleeve has a closed end attached to a distal segment of the elongate shaft and an open end. An outer section of the inverted sleeve that includes the open end is folded over onto an inner section of the inverted sleeve that includes the closed end at a rolling fold. An expansion device is supported on the elongate shaft at an axial location proximally spaced from the closed end and aligned with or distally spaced from the open end. The expansion device is configured for radially expanding the open end of the inverted sleeve.

In another aspect, a method of using a clot retrieval system is provided. The clot retrieval system includes a delivery catheter defining a lumen and having proximal and distal ends. An elongate shaft has proximal and distal ends and is configured for receipt within the delivery catheter. An inverted sleeve has a closed end attached to a distal segment of the elongate shaft and an open end. An outer section of the inverted sleeve that includes the open end is folded over onto an inner section of the inverted sleeve that includes the closed end at a rolling fold. An expansion device is supported on the elongate shaft at an axial location proximally spaced from the closed end and aligned with or distally spaced from the open end. The method includes a step of advancing the clot retrieval system in a collapsed configuration such that the open end of the inverted sleeve, the expansion device, and the rolling fold are distally spaced from a clot. According to the collapsed configuration, the expansion device is collapsed, the open end of the inverted sleeve is collapsed, and the rolling fold is at a first position. The method also includes steps of radially expanding the expansion device and radially expanding the open end of the inverted sleeve responsive to the step of radially expanding the expansion device. The open end of the inverted sleeve is then proximally retracted such that the open end of the inverted sleeve is proximally spaced from the clot, the rolling fold is proximally spaced relative to the first position of the rolling fold, and the clot is positioned radially between the elongate shaft and the outer section of the inverted sleeve.

BRIEF DESCRIPTION OF THE DRAWINGS

FIG. 3 is a partially sectioned side diagrammatic view of the clot retrieval system of FIG. 1, shown in a second expanded configuration; and FIG. 4 is a partially sectioned side diagrammatic view of the clot retrieval system of FIG. 1, shown being returned to the collapsed configuration after capturing a clot.

DETAILED DESCRIPTION

Figure 1:
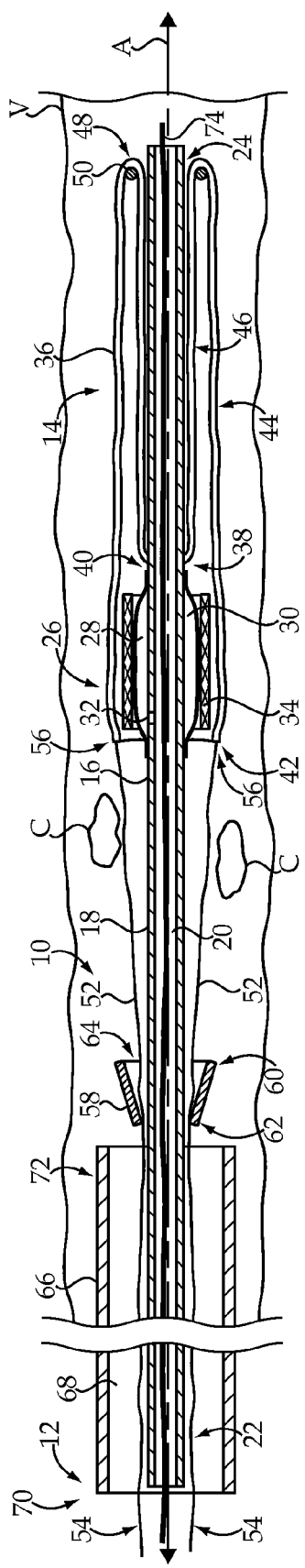
FIG. 1 is a partially sectioned side diagrammatic view of a clot retrieval system, according to one embodiment of the present disclosure, shown in a collapsed configuration.

Referring to FIG. 1, there is shown a clot retrieval system 10 according to one embodiment of the present disclosure. The clot retrieval system 10 may include a number of components, which may be provided within a sterile, tear open package, as is known in the art. In performing a clot retrieval procedure on a patient, some or all of the components of the clot retrieval system 10 may be used, depending upon the specifics of the procedure to be performed. As should be appreciated, however, the components shown in FIG. 1 might be separately packaged and/or the clot retrieval system 10 might also include components in addition to those shown, including components routinely used in percutaneous vascular procedures.

The clot retrieval system 10 has a proximal end 12 and a distal end 14, and includes an elongate shaft 16. According to the exemplary embodiment, the elongate shaft 16 may include an elongate tubular body 18 defining at least one lumen 20 extending from a proximal end 22 to a distal end 24 of the elongate tubular body 18. The elongate tubular body 18 may be made from any common medical tube material, such as, for example, polytetrafluoroethylene (PTFE), high density polyethylene (HDPE), nylon, polyetheretherketone (PEEK), or any vinyl, plastic, rubber, or silicone, and may exhibit both stiffness, or firmness, and flexibility. Materials as well as dimensions may vary depending on the particular application. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

An expansion device 26 is supported on the elongate shaft 16 and, according to the exemplary embodiment, may include a balloon 28, such as an inflatable balloon. As such, the lumen 20 referenced above may be an inflation lumen in fluid communication with an interior 30 of the balloon 28 via at least one opening 32 through the elongate tubular body 18. As should be appreciated, a fluid source may be used to inflate the balloon 28 via the inflation lumen 20 and opening 32. The expansion device 26 may also include an expandable stent 34 positioned over the balloon 28. The expandable stent 34 may be positioned and configured to radially expand responsive to expansion, or inflation, of the balloon 28 using known inflation media. Although a particular expansion device 26 is shown, it should be appreciated that one or more alternative devices capable of providing the radial expansion described herein may be substituted for one or both of the balloon 28 and the expandable stent 34.

The clot retrieval system 10 also includes an inverted sleeve 36 having a closed end 38 attached to a distal segment 40 of the elongate shaft 16 and an open end 42. An outer section 44 of the inverted sleeve 36 that includes the open end 42 is folded over onto an inner section 46 of the inverted sleeve 36 that includes the closed end 38 at a rolling fold 48. The inverted sleeve 36 may be made from a flexible film, such as, for example, a medical grade polyethylene film. As used herein, the "inverted sleeve" 36 includes any sleeve of material capable of being folded over onto itself. As the open end 42 is moved proximally or distally, the rolling fold 48 is similarly displaced. For example, if the open end 42 is moved proximally, the inner section 46 may shorten, the outer section 44 may lengthen, and the rolling fold 48 may have a more proximal position relative to the elongate shaft 16. If the open end 42 is moved distally, the outer section 44 may shorten, the inner section 46 may lengthen, and the rolling fold 48 may be moved distally. A ring 50, which is axially movable along the elongate shaft 16, may be positioned radially between the outer and inner sections 44, 46 of the inverted sleeve 36 and proximally spaced relative to the rolling fold 48 to assist in the rolling movement just described.

The open end 42 of the inverted sleeve 36 is positioned and configured such that radial expansion of the expansion device 26 expands the open end 42 in a radial direction. That is, the expansion device 26 may have an axial location, relative to longitudinal axis A, that is proximally spaced from the closed end 38 of the inverted sleeve 36, but is aligned with or distally spaced from the open end 42 of the inverted sleeve 36. Although not shown, one or more end stops may be provided on the elongate shaft 16 for restricting movement of the open end 42 of the inverted sleeve 36, such as by restricting axial movement of the ring 50. For example, an end stop may be positioned distally relative to the ring 50 and the rolling fold 48 to restrict distal movement of the ring 50 and the rolling fold 48 beyond the relative positions depicted in FIG. 1. This may also assist in providing desired initial positioning of the open end 42 of the inverted sleeve 36 relative to the expansion device 26.

The clot retrieval system 10 may also include at least one tether 52 having a free proximal end 54 positioned at the proximal end 12 of the clot retrieval system 10 and a distal end 56 attached to the open end 42 of the inverted sleeve 36. The tether 52 may be any metallic or non-metallic wire, string, thread, cable, cord, chain, fiber, etc. capable of proximally retracting the open end 42 of the inverted sleeve 36. The one or more tethers 52 may pass through a cone 58 supported on the elongate shaft 16. The cone 58 has a distal end 60 that is outwardly expanded, or radially expanded, relative to a proximal end 62 of the cone 58. The cone 58 may be proximally spaced relative to the expansion device 26 and may be stationary relative to the elongate shaft 16. The cone 58 may have at least one opening 64 or passage for receiving the one or more tethers 52 therethrough.

The elongate shaft 16 may be used in combination with a delivery catheter 66 defining a lumen 68 and having proximal and distal ends 70 and 72. The elongate shaft 16, and additional components described herein, may be configured for receipt within the delivery catheter 66. One or both of the delivery catheter 66 and the elongate shaft 16 may be configured for advancement through a vascular structure V of a patient over a wire guide 74 to gain access and provide proper placement of the clot retrieval system 10. For example, the delivery catheter 66 may be advanced over the wire guide 74, and then the wire guide 74 may be replaced with the elongate shaft 16. Alternatively, and as shown, the delivery catheter 66 and elongate shaft 16 may be advanced over the wire guide 74 and, more specifically, the wire guide 74 may be received within a lumen, such as lumen 20, of the elongate shaft 16. It should be appreciated that, according to some embodiments, the elongate shaft 16 may include separate inflation and wire guide lumens.

Although not shown, a handle may be provided at the proximal end 12 of the clot retrieval system 10. The handle may be attached to any one or more of the elongate shaft 16, the delivery catheter 66, and the one or more tethers 52 and may be used to facilitate relative movement of the components during a clot retrieval procedure. For example, to achieve the positioning and placement shown in FIG. 1, the elongate shaft 16 may be advanced distally beyond the open distal end 72 of the delivery catheter 66. The clot retrieval system 10 may be initially provided in a collapsed configuration in which the expansion device 26 is collapsed, the open end 42 of the inverted sleeve 36 is collapsed, and the rolling fold 48 is at a first position.

Figure 2:
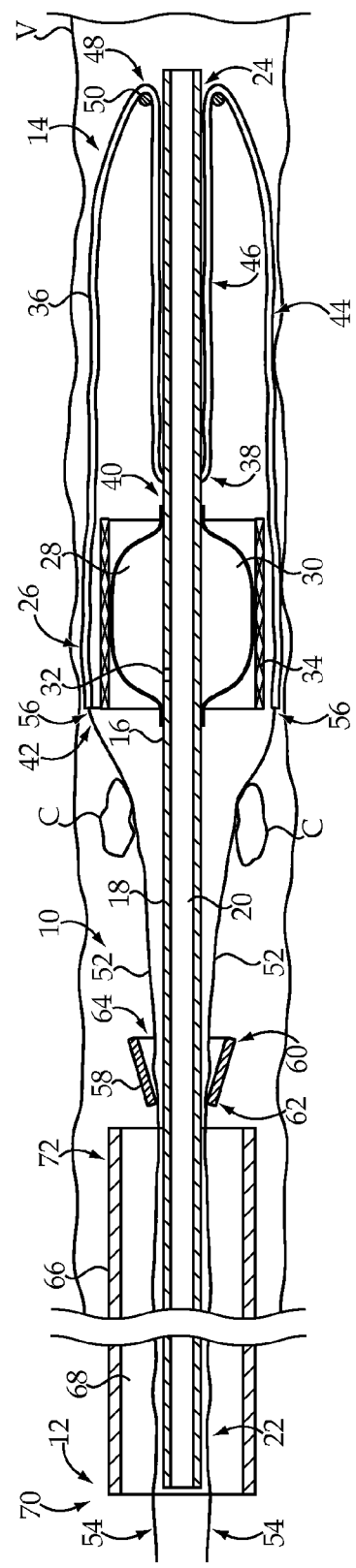
FIG. 2 is a partially sectioned side diagrammatic view of the clot retrieval system of FIG. 1, shown in a first expanded configuration.

The clot retrieval system 10 also has a first expanded configuration in which the expansion device 26 is radially expanded and the open end 42 of the inverted sleeve 36 is radially expanded, as shown in FIG. 2. According to the exemplary embodiment, the balloon 28 may be radially expanded and the expandable stent 34 may be radially expanded to achieve the first expanded configuration of the clot retrieval system 10. According to some embodiments, the open end 42 of the inverted sleeve 36 may be radially expanded to substantially match the inner diameter of the vascular structure V in which the clot retrieval system 10 is positioned.

As will be described below, the expansion device 26 and the open end 42 of the inverted sleeve 36 may be positioned distally relative to a clot C while the clot retrieval system 10 is positioned in the collapsed configuration. After transition of the clot retrieval system 10 to the first expanded configuration, the clot retrieval system 10 may be moved to a second expanded configuration, as shown in FIG. 3. According to the second expanded configuration, the expansion device 26 and open end 42 of the inverted sleeve 36 remain radially expanded, and the open end 42 of the inverted sleeve 36 and the rolling fold 48 are proximally refracted. According to the second expanded configuration, the clot C is positioned radially between the elongate shaft 16 and the outer section 44 of the inverted sleeve 36.

The expansion device 26 may then be collapsed, as shown in FIG. 4. For example, the balloon 28 may be collapsed, or deflated, in a manner known to those skilled in the art. During retraction of the open end 42 of the inverted sleeve 36, the one or more tethers 52 may be pulled through the cone 58 to assist in collapsing the expandable stent 34. That is, the one or more tethers 52 and, thus, the expandable stent 34, may be pulled in close proximity to the elongate shaft 16 using the cone 58. With the expansion device 26 collapsed and the open end 42 of the inverted sleeve 36 pulled radially inward to envelope the clot C, the elongate shaft 16 may be proximally retracted into the delivery catheter 66. The clot retrieval system 10 and clot C may then be removed from the patient.

INDUSTRIAL APPLICABILITY

Referring generally to FIGS. 1-4, a percutaneous vascular procedure using the clot retrieval system 10 of the present disclosure will be discussed with reference to a vascular structure V of a patient. The vascular structure V, as should be appreciated, may include a vessel wall defining a lumen and may have a region of blockage. That is, the region may include one or more clots C. A clinician may first use an introducer needle and wire guide 74 to gain access to the vascular structure V and position an introducer sheath in a known manner. Thereafter, the clot retrieval system 10 may be advanced over the wire guide 74 and toward the region of blockage. In particular, the clot retrieval system 10 may be advanced in the collapsed configuration such that the open end 42 of the inverted sleeve 36, the expansion device 26, and the rolling fold 48 are distally spaced from the clot C, as shown in FIG. 1. According to some procedures, the wire guide 74 and the elongate shaft 16 may be used to cross the clot C.

Next, as shown in FIG. 2, the clot retrieval system 10 may be moved from the collapsed configuration to the first expanded configuration. In particular, the balloon 28 and expandable stent 34 may be radially expanded to radially expand the open end 42 of the inverted sleeve 36. With the open end 42 fully expanded, the one or more tethers 52, or other suitable devices, may be proximally retracted to proximally retract the open end 42 of the inverted sleeve 36 over the clot C to move the clot retrieval system 10 to the second expanded configuration. According to the second expanded configuration, the open end 42 of the inverted sleeve 36, the rolling fold 48, and the ring 50 are all proximally retracted and the clot C is captured using the inverted sleeve 36.

The clot C may be removed from the patient by transitioning the clot retrieval system 10 back into the collapsed configuration and removing the clot retrieval system 10 from the patient. For example, the balloon 28 may be deflated and the expandable stent 34 may be collapsed to provide a lower profile of the elongate shaft 16. In addition, collapsing the open end 42 of the inverted sleeve 36 back toward the elongate shaft 16 may assist in capturing the clot C between the outer section 44 of the inverted sleeve 36 and the elongate shaft 16. According to some embodiments, it may be desirable to use a non-porous material for the inverted sleeve 36 so that no portions of the clot C may pass through the inverted sleeve 36. After capturing the clot C, the elongate shaft 16 may be proximally retracted into the delivery catheter 66 and the clot retrieval system 10 may be withdrawn from the vascular structure V.

The clot retrieval system 10 of the present disclosure may provide a relatively low profile and effective means for capturing and removing clots C from the vasculature of a patient. In particular, the clot retrieval system 10 disclosed herein may completely envelope the clots C in a confined space during retrieval from the patient, where conventional devices and systems often risk incomplete retrieval of clots or clot fragments.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A clot retrieval system, comprising:
   a delivery catheter defining a lumen and having proximal and distal ends;
   an elongate shaft having proximal and distal ends and configured for receipt within the delivery catheter;
   an inverted sleeve having a closed end attached to a distal segment of the elongate shaft and an open end, wherein an outer section of the inverted sleeve including the open end is folded over onto an inner section of the inverted sleeve including the closed end at a rolling fold;
   an expansion device supported on the elongate shaft at an axial location proximally spaced from the closed end and aligned with or distally spaced from the open end, wherein the expansion device is configured for radially expanding the open end of the inverted sleeve; and
   wherein the clot retrieval system is movable from a first expanded configuration characterized by the expansion device being axially positioned to expand the open end, to a second expanded configuration characterized by the open end being proximally displaced from a proximal end of the expansion device.

2. The clot retrieval system of claim 1, wherein the expansion device includes a balloon.

3. The clot retrieval system of claim 2, wherein the elongate shaft defines an inflation lumen in fluid communication with an interior of the balloon.

4. The clot retrieval system of claim 2, wherein the expansion device further includes an expandable stent positioned over the balloon.

5. The clot retrieval system of claim 1, further including at least one tether having a free proximal end positioned at a proximal end of the clot retrieval system and a distal end attached to the open end of the inverted sleeve.

6. The clot retrieval system of claim 5, further including a cone supported on the elongate shaft and having a distal end that is outwardly expanded relative to a proximal end of the cone, wherein the cone is proximally spaced relative to the expansion device and is configured to receive the tether.

7. The clot retrieval system of claim 1, wherein the inverted sleeve is non-porous.

8. The clot retrieval system of claim 1, wherein the elongate shaft includes a lumen configured for advancement over a wire guide.

9. A clot retrieval system, comprising:
   a delivery catheter defining a lumen and having proximal and distal ends;

an elongate shaft having proximal and distal ends and configured for receipt within the delivery catheter;

an inverted sleeve having a closed end attached to a distal segment of the elongate shaft and an open end, wherein an outer section of the inverted sleeve including the open end is folded over onto an inner section of the inverted sleeve including the closed end at a rolling fold;

an expansion device supported on the elongate shaft at an axial location proximally spaced from the closed end and aligned with or distally spaced from the open end, wherein the expansion device is configured for radially expanding the open end of the inverted sleeve; and a ring axially movable along the elongate shaft, wherein the ring is positioned radially between the inner and outer sections of the inverted sleeve and is proximally spaced relative to the rolling fold.

10. The clot retrieval system of claim 9, wherein the clot retrieval system has:

a collapsed configuration in which the expansion device is collapsed, the open end of the inverted sleeve is collapsed, and the rolling fold is at a first position; and an expanded configuration in which the expansion device is radially expanded, the open end of the inverted sleeve is radially expanded, and the rolling fold is proximally spaced relative to the first position.

11. A method of using a clot retrieval system, the clot retrieval system including a delivery catheter defining a lumen and having proximal and distal ends, an elongate shaft having proximal and distal ends and configured for receipt within the delivery catheter, an inverted sleeve having a closed end attached to a distal segment of the elongate shaft and an open end, wherein an outer section of the inverted sleeve including the open end is folded over onto an inner section of the inverted sleeve including the closed end at a rolling fold, and an expansion device supported on the elongate shaft at an axial location proximally spaced from the closed end and aligned with or distally spaced from the open end, and wherein the clot retrieval system is movable from a first expanded configuration characterized by the expansion device being axially positioned to expand the open end, to a second expanded configuration characterized by the open end being proximally displaced from a proximal end of the expansion device, the method comprising steps of:

advancing the clot retrieval system in a collapsed configuration such that the open end of the inverted sleeve, the expansion device, and the rolling fold are distally spaced from a clot, wherein, in the collapsed configuration, the expansion device is collapsed, the open end of the inverted sleeve is collapsed, and the rolling fold is at a first position;

radially expanding the expansion device;

radially expanding the open end of the inverted sleeve responsive to the step of radially expanding the expansion device; and proximally retracting the open end of the inverted sleeve such that the open end of the inverted sleeve is proximally spaced from the clot, the rolling fold is proximally spaced relative to the first position of the rolling fold, and the clot is positioned radially between the elongate shaft and the outer section of the inverted sleeve.

12. The method of claim 11, wherein the step of radially expanding the expansion device includes inflating a balloon.

13. The method of claim 12, wherein the step of radially expanding the expansion device further includes expanding an expandable stent positioned over the balloon.

14. The method of claim 13, wherein the step of proximally retracting the open end of the inverted sleeve includes proximally retracting at least one tether, wherein the tether has a free proximal end positioned at a proximal end of the clot retrieval system and a distal end attached to the open end of the inverted sleeve.

15. The method of claim 14, wherein the step of proximally retracting the open end of the inverted sleeve further includes proximally retracting the tether through a cone supported on the elongate shaft, wherein the cone is proximally spaced relative to the expansion device and has a distal end that is outwardly expanded relative to a proximal end of the cone.

16. The method of claim 15, further including deflating the balloon after the step of proximally retracting the open end of the inverted sleeve.

17. The method of claim 16, further including collapsing the expandable stent responsive to the step of proximally retracting the tether through the cone.

18. The method of claim 11, wherein the step of proximally retracting the open end of the inverted sleeve includes proximally sliding a ring along the elongate sleeve, wherein the ring is positioned radially between the inner and outer sections of the inverted sleeve and is proximally spaced relative to the rolling fold.

19. The method of claim 11, wherein the advancing step includes advancing the clot retrieval system over a wire guide.

20. The method of claim 19, wherein the advancing step further includes crossing the clot with the wire guide and the elongate shaft.

* * * * *